United States Patent
Kelley et al.

(10) Patent No.: US 10,039,653 B2
(45) Date of Patent: Aug. 7, 2018

(54) FABRIC COVERED POLYMERIC PROSTHETIC LINER

(71) Applicant: The Ohio Willow Wood Company, Mount Sterling, OH (US)

(72) Inventors: Christopher T. Kelley, Grandview Heights, OH (US); James M. Colvin, Hilliard, OH (US)

(73) Assignee: THE OHIO WILLOW WOOD COMPANY, Mount Sterling, OH (US)

( * ) Notice: Subject to any disclaimer, the term of this patent is extended or adjusted under 35 U.S.C. 154(b) by 130 days.

(21) Appl. No.: 15/050,095

(22) Filed: Feb. 22, 2016

(65) Prior Publication Data

US 2016/0166411 A1    Jun. 16, 2016

Related U.S. Application Data

(63) Continuation-in-part of application No. 14/020,165, filed on Sep. 6, 2013, now Pat. No. 9,265,629, which is a continuation-in-part of application No. 13/078,710, filed on Apr. 1, 2011, now abandoned.

(51) Int. Cl.
*A61F 2/78* (2006.01)
*A61F 2/80* (2006.01)
*A61L 27/16* (2006.01)
*A61L 27/02* (2006.01)

(52) U.S. Cl.
CPC .............. *A61F 2/7812* (2013.01); *A61F 2/80* (2013.01); *A61L 27/025* (2013.01); *A61L 27/16* (2013.01); *A61F 2/78* (2013.01)

(58) Field of Classification Search
CPC ... A61F 2/78; A61F 2/7812; A61F 2002/7818
See application file for complete search history.

(56) References Cited

U.S. PATENT DOCUMENTS

| | | | |
|---|---|---|---|
| 8,785,546 B2 * | 7/2014 | Jogo | C08F 8/04 524/534 |
| 2013/0331951 A1 * | 12/2013 | Doddroe | A61F 2/7812 623/36 |

OTHER PUBLICATIONS

Kuraray Europe; Alloy Technology for Extended Performance; (web address) www.kgk-rubberpoint.de; Kautschuk Gummi Kunststoffe; Sep. 2013, pp. 20-13; Kuraray Europe, BU Elastomer, Hattersheim, Germany; K 2013 Halle 07a / D06.
D. Kilian, et al; Two New HSBCs for Potential Medical Use; TPE Magazine, Apr. 2010, pp. 220-225.
Kuraray Co. Ltd.; Introduction of SEPTON(TM) J Series, New Development Polymer, SEPTON(TM) KL-J3341; Mar. 24, 2010; 7 pages.

(Continued)

*Primary Examiner* — Bruce E Snow
(74) *Attorney, Agent, or Firm* — Benesch Friedlander Coplan & Aronoff LLP

(57) ABSTRACT

A prosthetic cushion liner may include a fabric covering having an open end for introduction of a residual limb and a closed end opposite the open end. The prosthetic cushion liner may include a continuous layer of a gel composition residing on an interior surface of the fabric covering. The gel composition may include a plasticizing oil; one or more of a SEBS thermoplastic elastomer, a SEPS thermoplastic elastomer, a SEEPS thermoplastic elastomer; and a hydrogenated block copolymer.

23 Claims, 10 Drawing Sheets

(56) References Cited

OTHER PUBLICATIONS

Kuraray Co. Ltd.; Thermoplastic Elastomer SEPTON(TM); 1st Edition 2008. 3E; Ote Center Bldg., 1-1-3 Otemachi, Chiyoda-Ku, Tokyo 100-8115.
Kuraray Co. Ltd.; Thermoplastic Elastomer SEPTON(TM) V-Series; 1st Edition 2008. 3E; Ote Center Bldg., 1-1-3 Otemachi, Chiyoda-Ku, Tokyo 100-8115.
R. A. Shanks and I. Kong, "General Purpose Elastomers: Structure, Chemistry, Physics and Performance", Advances in Elastomers I: Blends and Interpenetrating Networks, 2013, pp. 11-45.

* cited by examiner

| TABLE 1: SEPTON™ J Series Representative Compound Properties | | | | |
|---|---|---|---|---|
| | Unit | Using SEPTON J Series | Using Existing SEPTON Product | Remarks |
| Hardness (Type A) (Shore OO) | | 0 14 | 0 28 | Flexibility, soft feel |
| Impact resilience rate | % | 36 | 71 | Shock-absorbing/vibration dampening properties |
| Melt flow rate 160 °C, 21N 200 °C, 21N | g/10min g/10min | 34 >400 | 3 76 | Low melt viscosity; high processability |
| Compression set 40 °C 70°C | % % | 9 59 | 10 51 | Mechanical performance on par with existing products |

(Data from Kuraray America, Inc.; Houston, Texas)

FIG. 5

| TABLE 2: SEPTON™ J Series Representative Compound Properties | | Compound 1 Approx. hardness 0 <Type A> | | Compound 2 Approx. hardness 15 <Type A> | |
|---|---|---|---|---|---|
| | | Using SEPTON™ J Series | Using existing SEPTON™ product | Using SEPTON™ J Series | Using existing SEPTON™ product |
| Hardness | Type A | 0 | 0 | 14 | 15 |
| | Type C | 8 | 15 | 43 | 45 |
| Compression Set 40 °C 70 °C | (%) | 9 | 10 | 11 | 15 |
| | (%) | 59 | 51 | 8 | 27 |
| Impact resilience rate | (%) | 36 | 71 | 36 | 57 |
| Melt flow rate 160 °C, 21N 160 °C, 21N | g/10min | 34 | 3 | -- | -- |
| | g/10min | -- | 6 | 3 | 1 |

(Data from Kuraray America, Inc.; Houston, Texas)

FIG. 6

| TABLE 3: Typical Properties of SEPTON™ V-Series | | | | | |
|---|---|---|---|---|---|
| Grade | | V9461 | V9475 | V9827 | Measurement Method |
| Type | | | | | |
| Hard Constituent Content | wt % | 30 | 30 | 30 | |
| Specific Gravity | | 0.89 | 0.89 | 0.90 | ISO 1183 |
| Hardness (Shore A) | | -- | -- | 78 | ISO 7619 |
| Tensile Properties | | | | | ISO 37 |
| 100% Modulus | MPa | -- | -- | 2.5 | |
| Tensile Strength | MPa | -- | -- | 24 | |
| Elongation | % | -- | -- | 560 | |
| Melt Flow Rate | | | | | ISO 1133 |
| 230 °C, 21N | g/10min | no flow | no flow | 3.5 | |
| 230 °C, 21N | g/10min | no flow | no flow | 6 | |
| Solution Viscosity | | | | | Toluene Solution 30 °C |
| 5 wt% | mPa*s | 90 | 240 | -- | |
| 10 wt% | mPa*s | -- | -- | 23 | |
| Physical Form | | powder | powder | pellet | |

(Data from Kuraray America, Inc.; Houston, Texas)

FIG. 7

| TABLE 4: SEPTON™ V-Series Representative Compound Properties | | 1 | 2 | 3 | Measurement Method |
|---|---|---|---|---|---|
| SEPTON™ V9461 | Parts by mass | 100 | 100 | 100 | |
| Process Oil | | 200 | 100 | 100 | |
| Polypropylene (homo MI = 1) | | 25 | 27.3 | 50 | |
| Organic Peroxide | | 4.6 | 3.5 | 4.6 | |
| Crosslink co-agent | | 8 | 6 | 8 | |
| Antioxidant | | 0.3 | 0.3 | 0.3 | |
| Hardness (Shore A) | | 37 | 61 | 78 | ISO 7619 |
| Tensile Properties | | | | | |
| 100% Modulus | MPa | 0.7 | 1.7 | 3.1 | ISO 37 |
| Tensile Strength | MPa | 2.9 | 6.7 | 8.4 | |
| Elongation | % | 420 | 470 | 400 | |
| Compression Set | | | | | |
| 70 °C, 22 h | % | 19 | 26 | 33 | ISO 7743 |
| 120 °C, 22 h | % | 21 | 26 | 37 | |
| Melt Flow Rate | | | | | |
| 210 °C, 98 N | g/10min | 11 | 7 | 27 | ISO 1133 |

(Data from Kuraray America, Inc.; Houston, Texas)

*FIG. 8*

TABLE 5: Composition of two examples

| MATERIAL | MINERAL OIL | J-SERIES | V-SERIES | PE |
|---|---|---|---|---|
| 1 | 75-85% | 15-20% | 0-5% | 0.1-0.5% |
| 2 | 75-85% | 0-5% | 15-20% | 0-0.5% |

(Total thermoplastic elastomer weight % may be 15-25%)

*FIG. 9*

TABLE 6: Composition and properties of examples

| # | Mineral Oil | SEPTON J | SEPTON 4033 | SEPTON 4055 | SEPTON 8004 | Hardener PE | Hardener PP | Shore 00 | Tear | Tensile | Modulus 50% | Modulus 100% |
|---|---|---|---|---|---|---|---|---|---|---|---|---|
| 1 | 78.1 | 21.9 | | | | | | 2.1 | X | X | X | X |
| 2 | 78.8 | 21.3 | | | | | | 4 | A | C | X | E |
| 3 | 80.8 | 9.6 | | 9.6 | | | | 5 | X | C | C | D |
| 4 | 77.5 | 22.5 | | | | | | 5.3 | X | X | X | X |
| 5 | 74.3 | 22.1 | 2 | | | | | 8 | B | C | X | D |
| 6 | 75.9 | 24.1 | | | | | | 9 | A | F | X | D |
| 7 | 74.3 | 24.1 | | | | | | 9.5 | A | C | X | D |
| 8 | 76.9 | 23.1 | | | | | | 10.5 | A | D | X | D |
| 9 | 76.3 | 22.1 | | | | 0.8 | | 10.1 | X | X | X | X |
| 10 | 77.5 | 20.9 | | | | 0.8 | | 10.8 | A | E | X | C |
| 11 | 74.3 | 20.1 | 4 | | | | | 11 | C | C | X | C |
| 12 | 77.2 | 21.6 | | | | 0.6 | | 11 | X | X | X | X |
| 13 | 77.4 | 7 | | 15.6 | | | | 11 | X | B | C | D |
| 14 | 75 | 25 | | | | | | 12 | A | C | X | D |
| 15 | 76.9 | 21.5 | | | | 0.8 | | 12.8 | X | X | X | X |
| 16 | 77.8 | 18.8 | 3 | | | | 0.4 | 13.9 | C | D | X | C |
| 17 | 77.5 | 18.7 | 3 | | | | 0.8 | 14 | C | D | X | D |
| 18 | 77.7 | 21.1 | | | | 1.21 | | 14 | X | D | B | B |
| 19 | 76.6 | 22.2 | | | | 0.6 | | 14.1 | X | X | X | X |
| 20 | 77.7 | 18.8 | 3 | | | | 0.5 | 14.3 | C | D | X | C |
| 21 | 76.6 | 21.4 | | | | 1 | | 14.5 | X | X | X | X |
| 22 | 77.4 | 18.7 | 3 | | | 0.4 | | 14.7 | B | D | X | C |
| 23 | 76.3 | 21.4 | | | | 1.2 | | 17.5 | X | X | X | X |
| 24 | 77.5 | 21 | | | | 1.5 | | 19 | X | A | A | B |
| 25 | 77.1 | 20.9 | | | | 1.99 | | 21 | X | C | A | A |
| 26 | 77.92 | 11 | | | 11 | | | 22 | D | F | X | B |

X – not tested; A, B, C, etc. – grade ranking, high to low

FIG. 10

FABRIC COVERED POLYMERIC PROSTHETIC LINER

CROSS-REFERENCE TO RELATED APPLICATIONS

This application is a Continuation-in-Part of U.S. patent application Ser. No. 14/020,165, filed on Sep. 6, 2013, which is a Continuation-in-Part of U.S. patent application Ser. No. 13/078,710, filed on Apr. 1, 2011, each of which are entirely incorporated by reference herein.

BACKGROUND

Polymeric prosthetic liners (or "liners") have become the interface of choice among amputees due to various beneficial characteristics thereof. These characteristics include, for example, comfort, security of suspension, protection of the residual limb, and ease of use. Modern liner technology allows amputees to employ a liner as the sole (stand-alone) interface between their residual limb (which is also commonly referred to as a residuum or amputation stump) and the interior of a prosthetic socket—in contrast to known wool or knit socks and cushioned socks or sheaths that must be worn in multiple layers and/or various combinations to provide sufficient cushioning and protection to a residual limb.

Prosthetic liners may be non-suspensory in nature. Non-suspensory liners are commonly referred to as "cushion liners." Prosthetic liners may optionally be suspensory in nature and may, therefore, include a docking element that facilitates suspension by mechanical attachment of the liner to the socket of a prosthesis. Suspensory liners are commonly referred to as "locking liners" or "cushion locking liner." Liners can be of standard "off-the-shelf" design, meaning the liner is of generic shape and will fit a range of residual limb shapes and sizes. Alternatively, liners may be custom designed for a particular amputee.

Liners may be comprised of various polymeric materials, including silicone, urethane, and thermoplastic elastomers (TPE) gels. Liners are now commonly made using various block copolymer and mineral oil gel compositions. Such polymeric materials, particularly block copolymer and mineral oil gel compositions, have proven themselves to provide an optimal level of comfort for most users.

It is also known to construct such liners with an outer layer of fabric. For example, the present assignee produces patented fabric-covered liners having an interior of exposed polymeric gel for contacting and cushioning an amputee's residual limb, and an integrated outer layer of fabric for, among other things, increasing the wear resistance of the liner, and facilitating donning/doffing and insertion of the liner-covered residual limb into a prosthetic socket.

As would be understood by one of skill in the art, liners as described above are frequently used by lower limb amputees. Lower limb amputees generally fall into one of two categories: above knee (AK) amputees and below knee (BK) amputees. In the case of a BK amputee, the knee joint is still present and, thus, a bending of the residual limb at the knee joint will still occur during ambulation. While the prosthetic hard socket of a BK prosthesis is generally recessed to accommodate the knee joint, BK amputees typically wear a liner that extends over the knee joint to some point along the thigh of the residual limb. Consequently, bending of the knee joint occurs under cover of the liner.

In a typical below-knee (BK) prosthesis an amputee's stump tends to "piston" in the socket: during ambulation the stump will come up in the socket of the prosthesis until the attaching means holding the prosthesis to the wearer causes the prosthesis to lift with the stump. On the way down, air may be trapped between the residuum and stump sock, or between the prosthesis socket and sock, or between a socket liner and a sock.

With wool and cotton socks which tend to breathe and which are not airtight, this pistoning effect is not a major problem with regard to the generation of sound effects. Since wool and cotton tend not to tightly form fit a residuum, the amputee typically packs a material around the residuum once it is placed into the prosthetic device or adds additional socks to increase thickness or puts on thicker socks in order to provide necessary fit. However, for socks which do not breathe and which are made from, e.g., polymeric material, a problem occurs when the residuum pistons in the prosthetic device: sound effects such as sucking and gurgling noises are generated which are obtrusive and inappropriate, often embarrassing the wearer. In addition, such air pockets produce non-uniform pressures and loading discontinuities on the skin, irritating it.

Finally, many amputees experience a swelling of the stump. When the residuum is in a prosthetic socket the stump tends to contract significantly, and when taken out of the socket the stump tends to expand within minutes of removal. This expansion and contraction of the residuum contributes to the development of air pockets and the generation of obtrusive noises since a sock which may have provided a comfortable fit on the expanded stump becomes a loose fit with air pocket opportunities when the residuum is placed inside the prosthetic socket. In addition, and over time, an amputee's residuum tends to adjust in size, usually shrinking. As these changes occur they increase the tendency for the pistoning effect, described above, to occur. In addition to the embarrassment caused by the sound effects generated by pistoning, cushioned socks which allow or promote air pocket formation quickly wear out and, if not replaced often, lead to lesions, etc. on the residuum.

Known cushioned residuum sheaths and socks are frequently purely tubular in shape, but may also be conical in shape. In either case, these devices often do not provide a form fit on an amputee's residuum. Further, regardless of whether such sheaths/socks are provided with internal and/or external cushioning material they frequently fail to avoid air pockets. While a stump may generally have a roughly conical or cubical shape there are invariably recessed areas on, e.g., the medial side of the prominent tibia bone. Generally, on the left side of a below knee residual limb, the recessed area will be predominantly on the right side of the tibia bone. There is also typically a smaller recessed area on the left side. For right side residual limbs the predominant recessed area is on the left side of the bone, with smaller recessed areas on the right side. Usually the greatest recess occurs immediately below the patella, on either side. In addition, left side amputees typically have a right side bias to the bony prominence of the below knee stump, and right side amputees have a similar bias to the left side. Conventional tubular or conical elastic socks simply cannot account for these several variable conditions without using extremely high levels of elastic tension which compress the outer-most points along the stump's circumference, causing discomfort and a non-uniform fit.

Amputees typically attach a prosthetic limb to their residual limb by means of a rigid socket, liner, and a suspension means. The rigid socket is often custom fabricated to match the shape of the intended user's residual limb and may be made of thermoplastic or fiber-reinforced thermoset materials, but can also be made from wood, metal, etc. Since such hard materials are generally uncomfortable when in intimate contact with the skin over long periods of time, especially under load bearing conditions, liners and/or prosthetic socks are often used as interface members between the hard socket and the residual limb to increase comfort. Early liners were commonly made of an open cell foam, such as Pelite or Kemblo, but were also made of silicone, urethane, etc., type of materials. See, for example, U.S. Pat. No. 5,258,037 and U.S. Pat. No. 5,376,132, both incorporated herein by reference. Prosthetic socks, as mentioned above, may be made of wool, cotton, synthetic materials, etc., and amputees tend to prefer liners and socks which are easily changed to facilitate cleaning, to accommodate volume changes in the residual limb, or to accommodate different user activities.

Suspension systems which help to hold a prosthetic limb in place may or may not be an integral part of the rigid socket and/or liner. Examples of suspension systems include supracondylar or waist belt, joint and corset systems, neoprene or latex sleeves, socket ears which grip the condyles, suction or pin and lock systems such as those where the pin is attached to a liner and the lock is attached to a hard socket, etc. Examples of various suspension systems may be found in U.S. Pat. No. 4,923,474, U.S. Pat. No. 4,923,475, U.S. Pat. No. 5,007,937, U.S. Pat. No. 5,108,456, U.S. Pat. No. 5,201,773, U.S. Pat. No. 5,201,774, U.S. Pat. No. 5,246,464, U.S. Pat. No. 5,263,923, U.S. Pat. No. 5,314,497, U.S. Pat. No. 5,387,245, U.S. Pat. No. 5,376,131 and U.S. Pat. No. 5,405,405, all incorporated herein by reference.

As block copolymer based prosthetic liners have become increasingly popular, it can be understood that further development of prosthetic liners using such materials would be desirable. The present invention is directed to such a further development.

SUMMARY

In one embodiment, a prosthetic cushion liner is provided. The prosthetic cushion liner may include a fabric covering. The fabric covering may include an open end for introduction of a residual limb. The fabric covering may include a closed end opposite the open end. The prosthetic cushion liner may include a continuous layer of a gel composition. The gel composition may reside on an interior surface of the fabric covering. The gel composition may include a plasticizing oil. The gel composition may include one or more of: a SEBS thermoplastic elastomer, a SEPS thermoplastic elastomer, and a SEEPS thermoplastic elastomer. The gel composition may include a hydrogenated block copolymer. The hydrogenated block copolymer may be derived from a living polymer represented by Formula (I):

$$B_1\text{-}A\text{-}B_2\text{---}X \qquad (I)$$

In Formula (I), A may represent a polymer block comprising a structural unit derived from a vinyl aromatic compound. $B_1$ and $B_2$ may each independently represent a polymer block comprising a structural unit derived from a conjugated diene compound. X may represent a linking group derived from reaction of an active terminal end of the living polymer with a coupling agent.

A better understanding of a prosthetic liner of the present invention can be gained by review of the following description of several exemplary embodiments thereof, along with the associated accompanying drawing figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

The accompanying figures, which are incorporated in and constitute a part of the specification, illustrate example methods and apparatuses, and are used merely to illustrate example embodiments.

FIG. 5 shows Table 1, listing representative compound properties;

FIG. 6 shows Table 2, listing representative compound properties;

FIG. 7 shows Table 3, listing representative compound properties;

FIG. 8 shows Table 4, listing representative compound properties;

FIG. 9 shows Table 5, listing composition of two examples; and

FIG. 10 shows Table 6, listing composition and properties of several examples.

DETAILED DESCRIPTION

In various embodiments, a prosthetic cushion liner is provided. The prosthetic cushion liner may include a fabric covering. The fabric covering may include an open end for introduction of a residual limb. The fabric covering may include a closed end opposite the open end. The prosthetic cushion liner may include a continuous layer of a gel composition. The gel composition may reside on an interior surface of the fabric covering. The gel composition may include a plasticizing oil. The gel composition may include one or more of: a SEBS thermoplastic elastomer, a SEPS thermoplastic elastomer, and a SEEPS thermoplastic elastomer. The gel composition may include a hydrogenated block copolymer. The hydrogenated block copolymer may be derived from a living polymer represented by Formula (I):

$$B_1\text{-}A\text{-}B_2\text{---}X \qquad (I)$$

In Formula I, A may represent a polymer block comprising a structural unit derived from a vinyl aromatic compound. $B_1$ and $B_2$ may each independently represent a polymer block comprising a structural unit derived from a conjugated diene compound. X may represent a linking group derived from reaction of an active terminal end of the living polymer with a coupling agent.

Figure 1A:
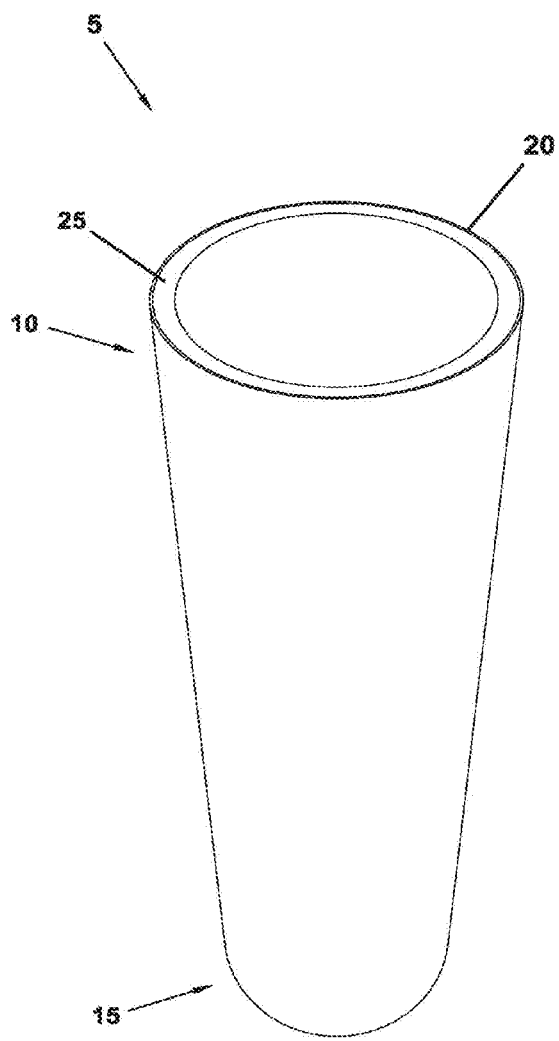
FIG. 1A shows an exemplary embodiment of a prosthetic liner of the present invention.
Figure 1B:
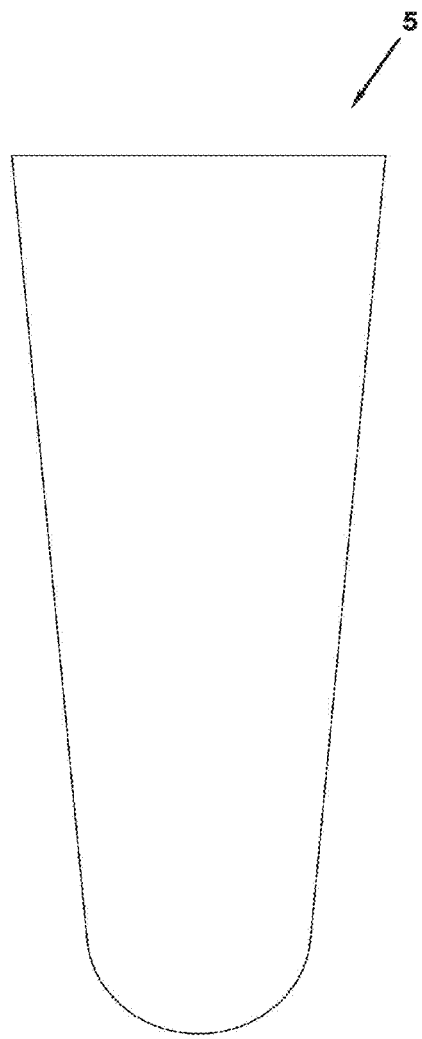
FIG. 1B shows an exemplary embodiment of a prosthetic liner of the present invention.
Figure 2:
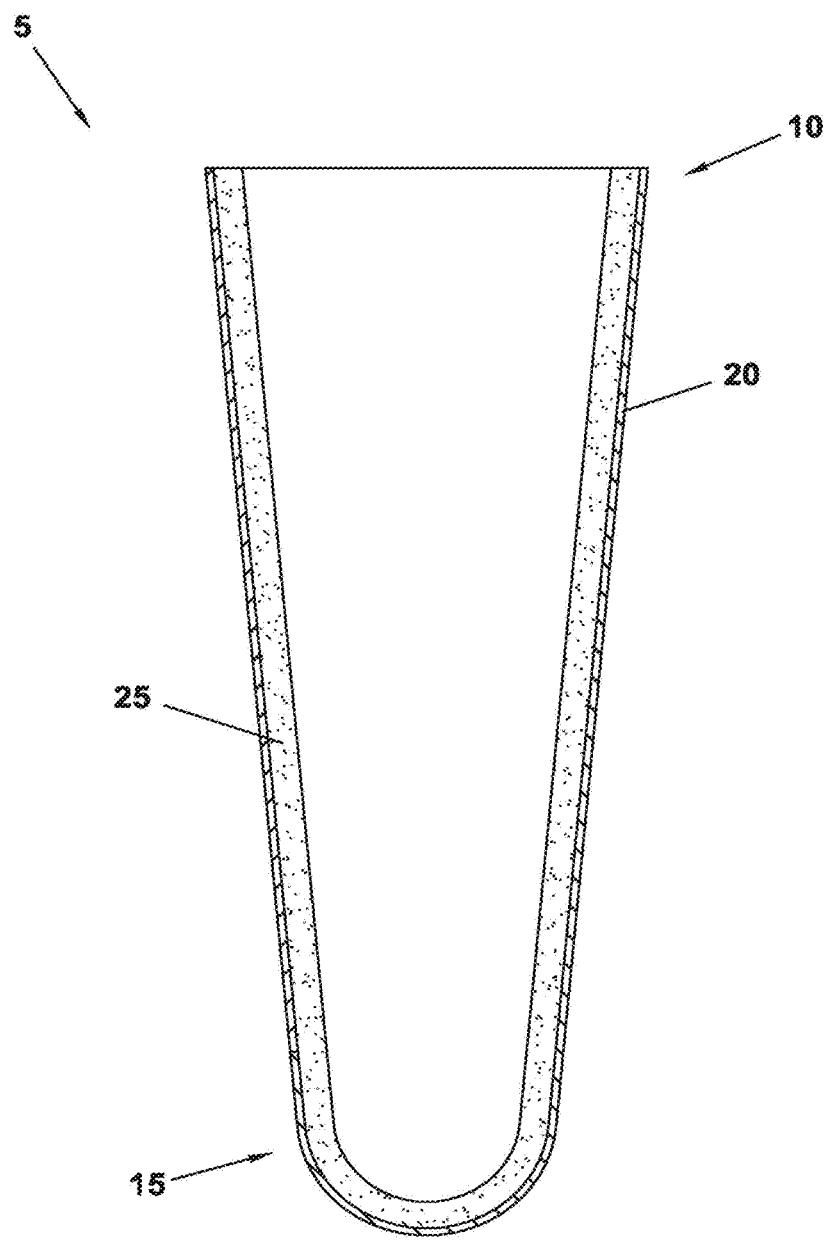
FIG. 2 is a cross-sectional view of an exemplary prosthetic liner of the present invention having a symmetric polymeric material distribution.
Figure 3:
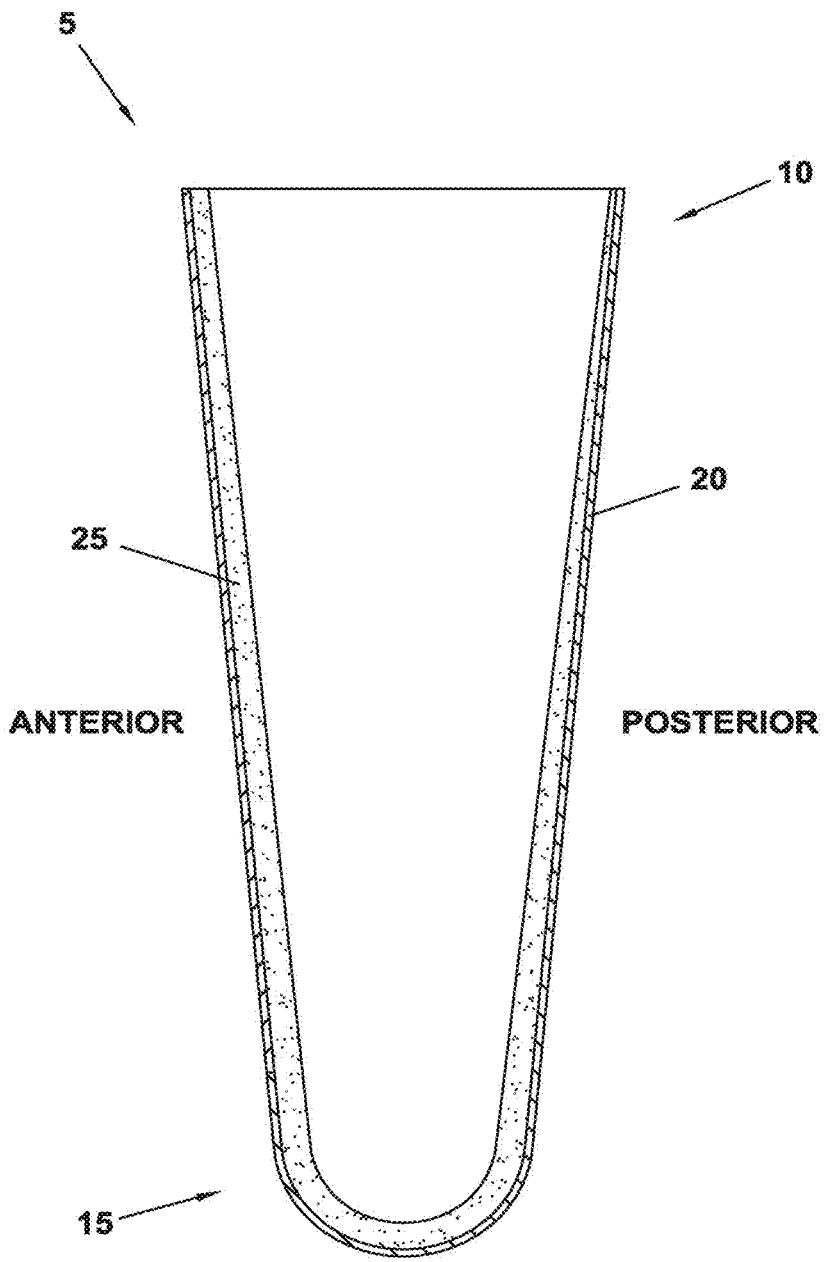
FIG. 3 is a cross-sectional view of an exemplary prosthetic liner of the present invention having an asymmetric polymeric material distribution.
Figure 4A:
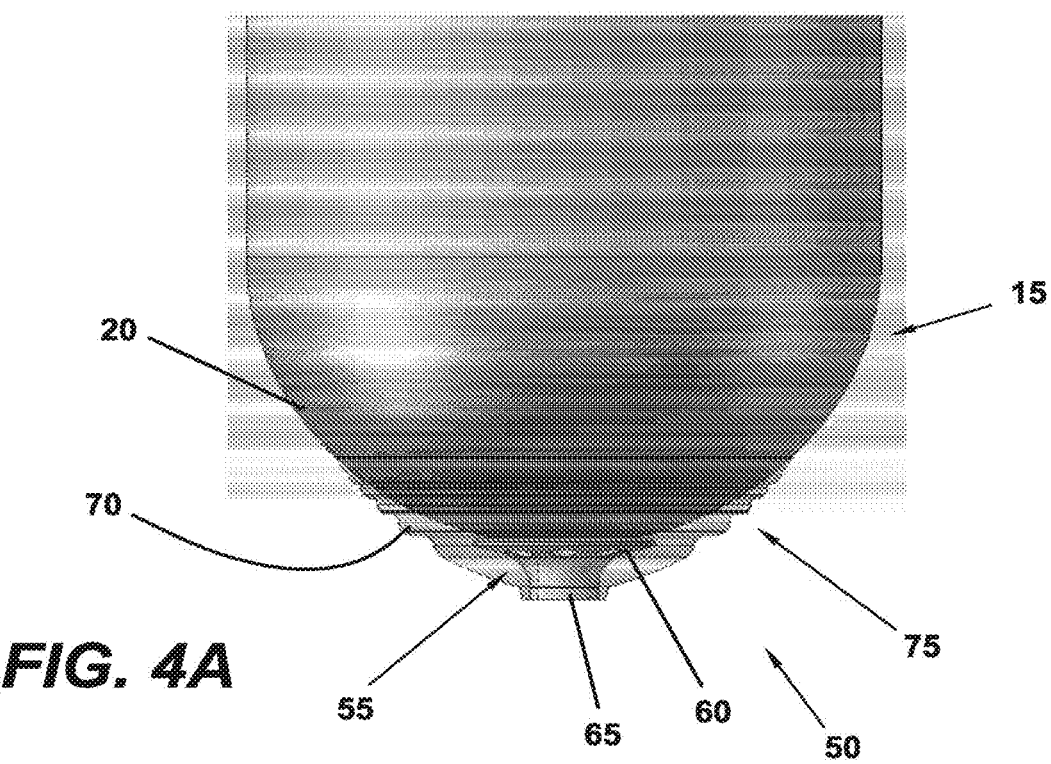
FIG. 4A is a detailed view in partial transparency of an exemplary docking element located at the closed end of a liner of the present invention.
Figure 4B:
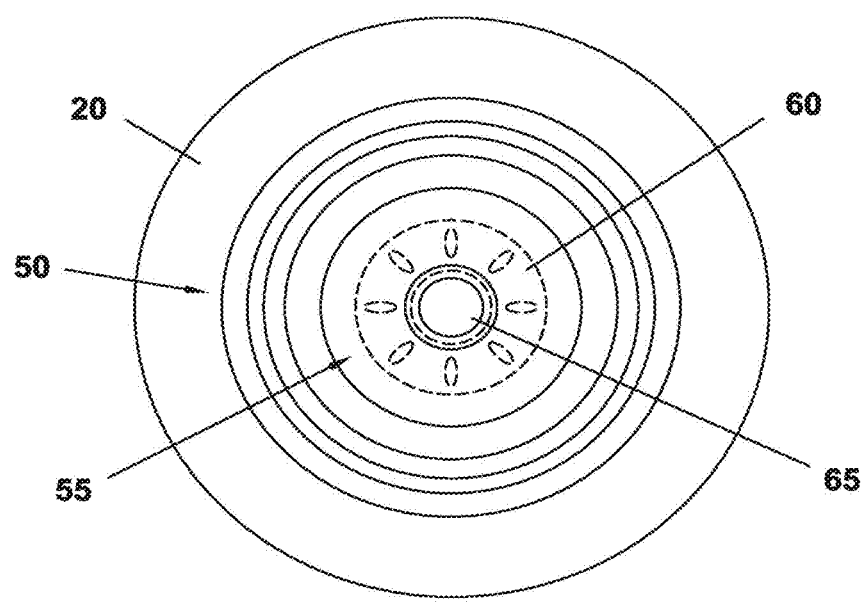
FIG. 4B is a bottom view of the docking element of FIG. 4A.

FIGS. 1A-1B and FIGS. 2-3 illustrate an embodiment of a below knee (BK) prosthetic cushion liner 5. FIGS. 4A-4B illustrate an embodiment of a cushion locking liner. The cushion locking liner may have the same or a similar fabric-gel construction as prosthetic cushion liner 5. Prosthetic cushion liner 5 and cushion locking liner may be hereinafter referred to simply as a "liner." While the liner shown in the drawings is a BK liner, liners may also be above knee (AK) liners for use by trans-femoral amputees.

Liner 5 may include an open end 10 for permitting insertion of a residual limb, and a closed end 15 opposite the open end. The interior of the liner may include a polymeric material 25 while the exterior of the liner may include a fabric covering 20. Polymeric material 25 of the liner interior may be in contact with the skin of a residual limb when the liner is worn. Fabric covering 20 of the liner exterior may be arranged to be in contact with the interior of a prosthetic socket when liner is used with a prosthetic limb.

Because polymeric material 25 of the liner interior may be in contact with the skin of a residual limb when the liner is worn, polymeric material 25 is generally smooth and continuous in nature such there are no seams or other discontinuities that may cause amputee discomfort. Typically, polymeric material 25 may extend completely to the edge of the fabric at the open end of the liner, such that the entire interior surface of the fabric covering 20 may be covered therewith. Alternatively, it is also possible that some length of fabric may remain devoid of polymeric material 25 so as to form a band or cuff of fabric at open end 10 of the liner. It is preferred, however, that polymeric material 25 may extend along fabric covering 20 to a length that is at least equivalent to the depth of a prosthetic socket cavity with which the liner may be used. Consequently, a liner may protect and cushion the entire portion of a residual limb residing in a prosthetic socket.

Fabric covering 20 of the liner may include various fabrics, preferably fabrics that are resistant to bleed-through of the underlying polymeric material 25. Preferably, but not necessarily, fabric 20 of the liner may include a stretch-controlling fabric that is used to control the overall longitudinal elasticity of liner 5. An explanation of such fabrics and the construction of a liner using such fabrics is described in U.S. patent application Ser. No. 12/711,234, filed May 4, 2010, which application is hereby incorporated by reference in its entirety. Other useable fabrics may include various stretchable non-woven materials and fiber-on-end fabrics such as WEARFORCE® composites (Xymid, LLC, Midlothian, Va.).

In many embodiments, polymeric material 25 may include a gel composition. The gel composition may include a hydrogenated block copolymer. The hydrogenated block copolymer may be derived from a living polymer represented by the Formula (I):

$$B_1\text{-}A\text{-}B_2\text{---}X \quad (I).$$

Group A of Formula (I) may include a polymer block of a structural unit derived from a vinyl aromatic compound. The vinyl aromatic compound may include, for example, one or more of: styrene, α-methyl styrene, 2-methyl styrene, 3-methyl styrene, 4-methyl styrene, 4-propyl styrene, 4-cyclohexyl styrene, 4-dodecyl styrene, 2-ethyl-4-benzyl styrene, 4-(phenylbutyl)styrene, vinyl toluene, 1-vinyl naphthalene, 2-vinyl naphthalene, and the like.

The hydrogenated block copolymer may include a mass percentage of A from about 25 to 50 based upon the mass of the hydrogenated block copolymer. The hydrogenated block copolymer may include a mass percentage of A of between about one of more of: 25 to 50, 37 to 50, 37 to 47, and 37 to 45. The hydrogenated block copolymer may include a mass percentage of A between any of the preceding values, for example, between about 36 to 44, 40 to 42, and the like. The hydrogenated block copolymer may include a mass percentage of A of about 40 based upon the mass of the hydrogenated block copolymer.

Polymeric blocks represented by $B_1$ and $B_2$ in Formula (I) may include a polymer block of a structural unit derived from a conjugated diene. The conjugated diene may include, for example, one or more of: 1,3-butadiene, isoprene, 2,3-dimethyl-1,3-butadiene, 1,3-pentadiene, 1,3-hexadiene, and the like.

The hydrogenated block copolymer may include a ratio of the mass of the polymer blocks $B_1$ and $B_2$ from about 0.10 to about 0.45. The hydrogenated block copolymer may include a ratio of the mass of the polymer blocks $B_1$ and $B_2$ of about one or more of: 0.10 to 0.45, 0.15 to 0.40, 0.20 to 0.35, and the like. The hydrogenated block copolymer may include a ratio of the mass of the polymer blocks $B_1$ and $B_2$ between any of the preceding values, for example, between about 0.17 to 0.25, 0.37 to 0.42, and the like.

In several embodiments, polymer blocks $B_1$ and/or $B_2$ may include one or more of branched and linear conjugated diene blocks. For example, $B_1$ may include 1,3-butadiene polymerized in a 1,2-carbon configuration, which may provide a vinyl branch. For example, B1 may include 1,3-butadiene polymerized in a 1,4-carbon configuration, which may provide a linear block including a 2,3-carbon alkene. For example, $B_2$ may include isoprene polymerized in a 1,2-carbon configuration, which may provide a vinyl branch. For example $B_2$ may include isoprene polymerized in a 1,4-carbon configuration, which may provide a linear block including a 2,3-carbon alkene. For example, $B_2$ may include isoprene polymerized in a 4,3-carbon configuration, which may provide an α-methyl vinyl branch. For example, $B_2$ may include isoprene polymerized in a 4,1-configuration, which may provide a linear block including a 2,3-carbon alkene.

In many embodiments, polymer blocks $B_1$ and/or $B_2$ may include at least 25% of branched blocks in order to prevent degradation of performance due to crystallization.

In various embodiments of the hydrogenated block copolymer, at least about 80% of alkenes corresponding to the one or more of the conjugated diene compounds may be hydrogenated. The hydrogenated block copolymer may include the alkenes of the polymer blocks derived from one or more of the conjugated diene compounds being hydrogenated by a percentage of about one or more of: 50, 55, 60, 65, 70, 75, 80, 85, 90, 95, and 100. The hydrogenated block copolymer may include the alkenes of the polymer blocks derived from one or more of the conjugated diene compounds being hydrogenated by a percentage between any of the preceding values, for example, between about 55 and about 75, between about 70 and about 90, between about 80 and 100, and the like.

The group X of Formula (I), may represent a linking group. The linking group may be derived from reaction of an active terminal end of the living polymer with a coupling agent. The coupling agent may include, for example, one or more of: divinyl benzene; a polyvalent epoxy compound, such as 1,2-polybutadiene, epoxidized soy bean oil, 1,3-bis (N,N-glycidyl aminomethyl)cyclohexane, and the like; halogenated silanes, such as dimethyldichlorosilane, dimethyl dibromosilane, trichlorosilane, methyl trichlorosilane, tetrachlorosilane, and the like; halogenated tin compounds, such as tin tetrachloride; ester compounds, such as methyl benzoate, ethyl benzoate, phenyl benzoate, diethyl oxalate, diethyl malonate, diethyl adipate, dioctyl adipate, dimethyl phthalate, diethyl phthalate, dimethyl isophthalate, dimethyl terephthalate, and the like; carbonate ester compounds, such as dimethyl carbonate, diethyl carbonate, diphenyl carbonate, and the like; and alkoxysilane compounds, such as dimthyldimethoxylsilane, methyl trimethoxysilane, methyl triethoxysilane, tetramethoxysilane, tetraethoxysilane, bis(trimethoxysilyl)hexanse, bis(triethoxysilyl)ethane, and the like.

The reaction of the coupling agent with group X of the living polymer to provide the hydrogenated block copolymer precursor may include a coupling efficiency of at least about 50%. The reaction of the coupling agent with X of the living polymer to provide the hydrogenated block copolymer precursor may include a coupling efficiency of at least about one or more of: 50%, 60%, 70%, 80%, 90%, and 99%.

The hydrogenated block copolymer may include an average molecular weight between about 50,000 to about 1,000,000. The hydrogenated block copolymer may include an average molecular weight between about one or more of: 50,000 to 1,000,000, 100,000 to 800,000, 200,000 to 600,000, and the like. The hydrogenated block copolymer may include an average molecular weight between any of the preceding values, for example, between about 200,000 and about 900,000, between about 75,000 and about 800,000, and the like.

The hydrogenated block copolymer may be formulated with a non-aromatic rubber softener. The non-aromatic rubber softener may include one or more of: mineral oils, such as paraffinic process oil and naphthenic process oil; vegetable oils, such as peanut oil and rosin; phosphate esters; low-molecular weight polyethylene glycol; liquid paraffin; synthesis oils, such as low-molecular weight ethylene, ethylene-α-olefin copolymerized oligomer; liquid polybutene; liquid polyisoprene or hydrogenated products thereof; poly butadiene or hydrogenated products thereof; and the like.

The non-aromatic rubber softener may be present at a ratio from about 170 to about 2,000 mass parts based upon 100 mass parts of the hydrogenated block copolymer. The non-aromatic rubber softener may be present at a ratio based upon 100 mass parts of the hydrogenated block copolymer of about one or more of: 170 to 2,000, 200 to 1,500, 250 to 1,300, and the like. The non-aromatic rubber softener may be present at a ratio based upon 100 mass parts of the hydrogenated block copolymer between any of the preceding values, for example, between about 200 to 500, between about 1,300 and about 1,700, and the like.

The hydrogenated block copolymer may include or be a SEPTON™_J-series thermoplastic elastomer (Kuraray America, Inc.; Houston, Tex.). The hydrogenated block copolymer may include any hydrogenated block copolymer described in U.S. Pat. No. 8,785,546, which is incorporated by reference in its entirety.

The hydrogenated block copolymer may be characterized by a specific gravity of about 0.90 to about 0.95. The hydrogenated block copolymer may be characterized by a specific gravity of about 0.93.

The hydrogenated block copolymer may include A, B$_1$, and B$_2$ in any order, e.g., block, random, and the like.

The hydrogenated block copolymer may be present in the gel composition in an amount between about 3 weight percent and about 25 weight percent. The hydrogenated block copolymer may be present in the gel composition in a weight percentage amount of one or more of: 1, 3, 5, 10, 15, 17, 20, 23, and 25. The hydrogenated block copolymer may be present in the gel composition between any of the preceding values, for example between about 3 and about 5, between about 10 and about 20, and the like. The hydrogenated block copolymer may be present in the gel composition in an amount less than 1%. The hydrogenated block copolymer may be present in the gel composition in an amount in weight percentage of less than about one or more of 20, 15, and 10. The hydrogenated block copolymer may be present in the gel composition in an amount of about 19%.

In some embodiments, the gel composition may further include one or more of: a SEBS thermoplastic elastomer, a SEPS thermoplastic elastomer, and a SEEPS thermoplastic elastomer. The SEBS thermoplastic elastomer may include an at least partially hydrogenated polybutadiene polymer terminated with styrene monomers (S), i.e. a hydrogenated styrenic polybutadiene block copolymer. The butadiene polymer blocks may be one or more of: linear and branched. The configuration of the butadiene polymer blocks may be polymerized to ordered blocks, random, or a combination of both ordered and random. The SEBS thermoplastic elastomer may be represented by Formula (II):

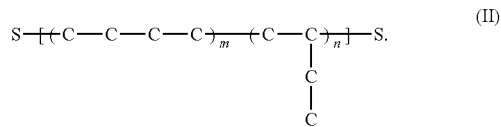

The SEPS thermoplastic elastomer may include an at least partially hydrogenated polyisoprene polymer terminated with styrene monomers (S), i.e., a hydrogenated styrenic polyisoprene block copolymer. The isoprene polymer blocks may be polymerized in a 1,2 carbon configuration, a 3,4 carbons configuration, or a mixture of both 1,2- and 3,4-carbon configuration. The SEPS thermoplastic elastomer may be represented by Formula (III):

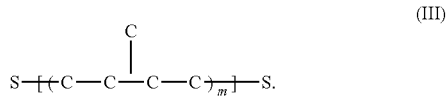

The SEEPS thermoplastic elastomer may include an at least partially hydrogenated poly(isoprene/butadiene) copolymer terminated with styrene monomers (S), i.e., a hydrogenated styrenic polyisoprene polybutadiene block copolymer. The isoprene polymer blocks may be polymerized in a 1,2 carbon configuration, a 3,4 carbons configuration, or a mixture of both 1,2- and 3,4-carbon configuration. The butadiene polymer blocks may be one or more of: linear and branched. The configuration of one or more of the isoprene polymer blocks and the butadiene polymer blocks may be polymerized in ordered blocks, random, or a combination of both ordered and random. The SEEPS thermoplastic elastomer may be represented by Formula (IV):

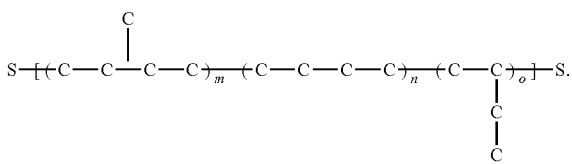

(IV)

In several embodiments, the gel composition may include a hydrogenated block copolymer, as defined by Formula (I), and a SEBS thermoplastic elastomer, as defined by Formula (II). The SEBS thermoplastic elastomer may include one or more SEPTON™ 8000 series, e.g. 8004, 8006, 8007, 8076, and 8104 (Kuraray America, Inc.; Houston, Tex.).

In some embodiments, the SEBS thermoplastic elastomer may include a styrene content of between about 27 weight percent and about 65 weight percent. The SEBS thermoplastic elastomer may include a styrene content of about 30 weight percent. The SEBS thermoplastic elastomer may include a styrene content of about 31 weight percent. The SEBS thermoplastic elastomer may include a styrene content of about 33 weight percent. The SEBS thermoplastic elastomer may include a styrene content of about 60 weight percent.

In some embodiments, the SEBS thermoplastic elastomer may include a specific gravity between about 0.90 and about 0.98. The SEBS thermoplastic elastomer may include a specific gravity of about 0.91. The SEBS thermoplastic elastomer may include a specific gravity of about 0.92. The SEBS thermoplastic elastomer may include a specific gravity of about 0.97.

In several embodiments, the hydrogenated block copolymer and the SEBS thermoplastic elastomer may be present together in the gel composition in a ratio between about one or more of: 11:1, 6:1, 5:1, 3:1, 2:1, 1:1, 1:2, 1:4, and 1:7.

In many embodiments, the gel composition may include a hydrogenated block copolymer, as defined by Formula (I), and a SEPS thermoplastic elastomer, as defined by Formula (III). The SEPS thermoplastic elastomer may include one or more SEPTON™ 2000 series, e.g. 2002, 2004, 2005, 2006, 2063, and 2104 (Kuraray America, Inc.; Houston, Tex.).

In some embodiments, the SEPS thermoplastic elastomer may include a styrene content of between about 10 weight percent and about 70 weight percent. The SEPS thermoplastic elastomer may include a styrene content of between about 13 weight percent and about 20 weight percent. The SEPS thermoplastic elastomer may include a styrene content of between about 30 weight percent and about 36 weight percent. The SEPS thermoplastic elastomer may include a styrene content of about 65.

In some embodiments, the SEPS thermoplastic elastomer may include a specific gravity between about 0.85 and about 1.0. The SEPS thermoplastic elastomer may include a specific gravity of about 0.89. The SEPS thermoplastic elastomer may include a specific gravity of about 0.91. The SEPS thermoplastic elastomer may include a specific gravity of about 0.92. The SEPS thermoplastic elastomer may include a specific gravity of about 0.98.

In several embodiments, the hydrogenated block copolymer and the SEPS thermoplastic elastomer may be present together in the gel composition in a ratio between about one or more of: 11:1, 6:1, 5:1, 3:1, 2:1, 1:1, 1:2, 1:4, and 1:7.

In many embodiments, the gel composition may include a hydrogenated block copolymer, as defined by Formula (I), and a SEEPS thermoplastic elastomer, as defined by Formula IV. The SEEPS thermoplastic elastomer may include one or more SEPTON™ 4000 series, e.g. 4033, 4044, 4055, 4077, 4099, and HG252 (Kuraray America, Inc.; Houston, Tex.).

In some embodiments, the SEEPS thermoplastic elastomer may include a styrene content of between about 27 weight percent and about 35 weight percent. The SEEPS thermoplastic elastomer may include a styrene content of about 30 weight percent. The SEEPS thermoplastic elastomer may include a styrene content of about 32 weight percent.

In some embodiments, the SEEPS thermoplastic elastomer may include a specific gravity between about 0.90 and about 0.95. The SEEPS thermoplastic elastomer may include a specific gravity of about 0.91.

In some embodiments, the SEEPS thermoplastic elastomer may be present in the gel composition in an amount in weight percent of one or more of: 1, 2, 3, 5, 7, 10, 12, 15, 18, and 20. The SEEPS thermoplastic elastomer may be present in the gel composition in a amount in weight percent between any of the preceding values, for example, between about 3 and about 5, between about 2 and about 12, and the like. The SEEPS thermoplastic elastomer may present in about 3 weight percent. The SEEPS thermoplastic elastomer may be present in an amount less than 1 weight percent.

In several embodiments, the hydrogenated block copolymer and the SEEPS thermoplastic elastomer may be present together in the gel composition in a ratio between about one or more of: 11:1, 6:1, 5:1, 1:1, 1:2, 1:4, and 1:7.

In several embodiments, the gel composition may include a plasticizing oil. The plasticizing oil may include mineral oil or a purified mineral oil, e.g., USP grade mineral oil. The plasticizing oil may be present in the gel composition in an amount between about 75 weight percent and about 85 weight percent based on the total gel composition.

In some embodiments, the gel composition may include a hardening agent. The hardening agent may include one or more of polyethylene, polypropylene, and styrene oligomers, e.g., PICCOLASTIC™ (Eastman Chemical Corp., Kingsview, Tenn.). The hardening agent may include polyethylene. The gel composition may include the hardening agent in an amount between about 0.1 weight percent and about 1.5 weight percent based on the total gel composition. The gel composition may include the hardening agent in an amount of up to about 5 weight percent.

In many embodiments, the gel composition may include a Shore 00 hardness, i.e., durometer value, of about one of, or one or more of: 9, 10, 11, 12, 13, 14, 15, 16, 17, 18, 19, 20, 21, 22, 23, 24, 25, 26, 27, 28, 29, 30, 31, 32, 33, 34, and 35, or a range between any two of the preceding values, for example, between about 10 and about 35, between about 15 and 35, and the like.

In some embodiments, the gel composition may include other ingredients such as, without limitation, antioxidants, light stabilizers, UV-absorbents, lubricants, fillers, anti-clouding agents, colorants, flame retardants, anti-statics, electrifying agents, antibacterial agents, anti-mold agents, foaming agents, skin conditioning agents, astringents, biocides, medicaments, and the like.

The gel composition may include an amount of a hydrogenated block copolymer, e.g., a SEPTON™ J-Series copolymer as described herein. The gel composition maybe include an amount of a SEEPS or SEBS thermoplastic elastomer including cross-linkable hard blocks, e.g., styrene blocks. The SEEPS or SEBS thermoplastic elastomer including cross-linkable hard blocks may be denoted S*EEPS* or S*EBS*, respectively. The cross-linkable hard blocks may be effective to vulcanize or cross-link by reaction with organic peroxides or electron beam technology. The S*EEPS* thermoplastic elastomer may include a SEPTON™ V-Series, e.g. V9461 and V9475 (Kuraray America, Inc.; Houston, Tex.). The S*EBS* thermoplastic elastomer may include a SEPTON™ V-Series, e.g., V9827 (Kuraray America, Inc.; Houston, Tex.). The gel composition may include an of a SEPTON™ Q-Series thermoplastic elastomer (Kuraray America, Inc.; Houston, Tex.). The gel compositions may also include some amount of an additional thermoplastic elastomer(s) such as, without limitation, another SEPTON™ thermoplastic elastomer, as described herein. The additional thermoplastic elastomer may function, at least in part, as a detackifying agent.

The SEPTON™ J-Series material incorporates hydrogenated styrenic block copolymers, as described herein, and exhibits extremely low-hardness gel material to produce a composition that is particularly well-suited for use in a gel-based prosthetic liner. According to the Kuraray website as of the date of this filing, advantageous properties of the J-Series thermoplastic elastomers include: high plasticity; high strength and superior mechanical performance including: compression set and tear resistance; high molten liquidity, which is excellent for polymer processing; superior shock-absorption and vibration dampening performance; soft feel; excellent low-temperature properties; and low density/weight savings. Further exemplary J-Series compound characteristics are provided in FIG. 5, Table 1 and FIG. 6, Table 2.

The SEPTON™ V-Series material, as described herein, also incorporates hydrogenated styrenic thermoplastic elastomers, but with a reactive/cross-linkable hard block and soft block. The V-series material is characterized as exhibiting exhibits excellent heat resistance and durability, while simultaneously possessing good elasticity and the ability to produce a low hardness compound (e.g., Shore 30A). The V-series material is also characterized as providing good miscibility with polyolefins and styrenic resins, having a low specific gravity, and good low temperature properties. Further exemplary V-Series elastomer properties and associated exemplary compound characteristics are provided in FIG. 7, Table 3 and FIG. 8, Table 4.

The SEPTON™ Q-Series material also incorporates thermoplastic elastomers, and is particularly well-suited to the design of polymer alloys. The Q-series exhibits excellent abrasion and scratch resistance, while being very lightweight and having excellent adhesion over olefinic materials. The Q-series material is also characterized as exhibiting superior hydrolysis resistance.

A composition of the invention includes some amount of one or a combination of J-Series, V-Series and/or Q-Series materials, in conjunction with a number of other materials that may be provided for compounding, tackifying or other material property altering purposes. Such materials may include, without limitation, mineral and or other plasticizing oils, polyethylene (PE), antioxidants, other skin conditioning agents, astringents, biocides, medicaments, etc.

The general composition of two exemplary and non-limiting examples of block copolymer and plasticizing oil gel materials according to the invention are shown in FIG. 9, Table 5. Other non-listed materials may also be present in various amounts.

A gel composition that includes J-Series, V-Series and/or Q-Series material may have varying degrees of hardness. It has been found, however, that a gel composition having a hardness of between about 15-35 on the Shore 00 scale should provide optimal comfort for most users. Various amounts of PE may be added to adjust the hardness in some embodiments. The thickness of the polymeric layer of a liner of the present invention is preferably between about 0.150-0.50 inches, but may be thicker in some cases.

At least three standard geometries may be provided for both the exemplary cushion liners and the exemplary cushion locking liners. These geometries may be a uniform wall (as exemplified in FIG. 2), a tapered wall (as exemplified in FIG. 3), and a contoured wall (not shown). A recessed configuration in which a localized thinning of the gel in the area of the liner that will overlie the back of the knee or the elbow crease is also possible in all liner embodiments.

The uniform wall cushion and cushion locking liner simply comprise a uniform thickness of gel. Tapered wall cushion liner and cushion locking liners are generally those having a layer of gel which is thicker distally for additional padding (and because most shrinkage of the residual limb occurs at this point of the limb) and thinner proximally (near the open end of the liner to blend in and interface more easily with the residual limb. The taper may be uniform along both the anterior or posterior sides of the liner, or may be more pronounced along the posterior side (as shown in FIG. 3). Contoured wall cushion liners and cushion locking liners have an uneven distribution of gel throughout to provide cushion effects where needed and, in exemplary embodiments, have a thinner posterior middle and upper to allow maximum range of motion optionally with a thicker distal end both anterior—medial and anterior—later with less thickness in the region between these two areas so as to pad typical bony prominences. Contoured wall liners are often thicker distally and custom shapes can easily be provided to satisfy the individual user.

Liners of the present invention may also be of multi-layer polymeric construction. Such a construction is described in U.S. patent application Ser. No. 12/407,362, filed Mar. 19, 2009 and 61/037,765, filed Mar. 19, 2008, both of which are incorporated by reference herein.

Cushion locking liners of the present invention include a connecting (attachment) element for coupling the distal end of the liner to the socket of a prosthesis. The connecting element may be of various design, as evidenced by the line of locking liners previously and currently available from the application assignee, The Ohio Willow Wood Company.

One particular exemplary embodiment of a connecting element 50 of the present invention is illustrated in FIGS. 4A-4B. This connecting element 50 includes a metallic threaded T-nut 55 that is attached to the fabric 20 of the liner at the closed end 15 thereof by an overlying and substantially encasing semi-flexible umbrella 70.

As shown, the T-nut 55 portion of the connecting element 50 includes a base portion 60 from which extends a hollow, internally-threaded boss 65. Preferably, at least the interior surface of the base portion 60 of the T-nut 55 is concave so as to better conform to the rounded distal shape of the liner once a residual limb is inserted therein. The threaded boss 65 is provided to receive and retain a like-threaded pin, lanyard connector or other connecting element (not shown) that can be used to attach the liner to a mating coupling component associated with a socket of a prosthesis. Such connecting elements are well known to those of skill in the art.

The encasing umbrella portion 70 of the connecting element 50 may be comprised of polyurethane, which bonds to the fabric at the closed end of the liner and secures the T-nut 55 in position thereon. It may also be possible to substitute a hard silicone rubber or another similar material for the umbrella 70. The design of this umbrella 70 differs from known designs in that this umbrella is preferably provided with an accordion configuration. That is, as best shown in FIGS. 4A-4B, the umbrella 70 has a stepped configuration 75 that allows for a slight collapse or compression of the umbrella as the weight of an amputee presses the closed end of an associated liner into the bottom of the prosthetic socket. By allowing for a slight collapse or compression of the umbrella 70, the connecting element 50 is able to better conform to the shape of a residual limb, thereby providing increased comfort for amputees. Other locking liners may use an umbrella of other than the depicted accordion configuration, such as an umbrella, of smooth configuration.

Liners of the present invention may be donned by inversion and rolling such that the polymeric material does not drag against the skin. In this manner, the cushioning polymeric material encloses the limb and/or device without sliding or friction. The fabric exterior slides against itself, preventing the sticking together of the polymeric material. Therefore, no lubricant, talcum powder, etc. is required during donning. A liner of the present invention may be doffed (removed) by simply unrolling it from the residual limb.

If desired, the polymeric material may include antioxidants such as Vitamins A, B and C or any other antioxidants commonly used in polymers and which can weep out on a time release basis. In addition, skin conditioning agents may be added to the polymeric material to soothe the skin during wear. Such skin conditioners may include mineral oil, baby oil, etc., which may be added to the polymeric material prior to its application to the fabric. Astringents, biocides, medicaments, etc., may be added or applied to the polymeric material to prohibit infection, heal sores on the residuum, etc.

Manufacturing of a liner of the present invention obviously involves application of the polymeric material to the fabric. This process may occur by dipping, spraying, brushing, rolling, etc. Preferably, but not necessarily, liners of the present invention are manufactured by compression molding using a female die cavity, and a male mold core over which the fabric is placed before insertion of the core into the cavity. It may be possible to similarly produce a liner of the present invention by injection molding.

A prosthetic cushion liner and cushion locking liner may be designed to enclose at least a portion of a residual limb that may be located in a prosthetic socket. As such, a liner may include an open end for allowing introduction of the residual limb, and a closed end opposite the open end. The closed end may abut and cushion a distal end of the residual limb when the liner is worn. Such a liner may be used by an upper or lower extremity amputee.

A liner of the present invention may include a polymeric material with a fabric outer covering. As such materials have proven to be especially effective at cushioning and protecting residual limbs while simultaneously providing amputees with a high level of comfort, the polymeric material used in a liner of the present invention may include a block copolymer and plasticizing (e.g., mineral) oil gel composition, which may include additional ingredients such as, without limitation, Vitamin E. More particularly, the block copolymer and mineral oil gel compositions used in a liner may include some amount of one or a combination of Septon™ J-Series thermoplastic elastomer. Septon™ V-series thermoplastic elastomer, and/or Septon™ Q-Series thermoplastic elastomer.

The J-Series thermoplastic elastomer mentioned above may incorporate hydrogenated styrenic thermoplastic elastomers and extremely low-hardness gel material to produce a compound that may be suited for use in a block copolymer and mineral oil gel-based prosthetic liner. The V-Series thermoplastic elastomer may also be a hydrogenated styrenic elastomer, and may include cross-linkable hard blocks. Such cross-links may produce compounds with higher than normal heat and oil resistance. The Q-series thermoplastic elastomer may be suited to the design of polymer alloys.

Once constructed, a prosthetic liner may include a polymeric material interior and a fabric exterior. When used with a prosthesis, the polymeric material of the liner interior may be in contact with the skin of a residual limb and the fabric exterior may be in contact with the interior of a prosthetic socket.

Because the polymeric material of the liner interior may be in contact with the skin of a residual limb when the liner is worn, the polymeric material may be smooth and continuous in nature such that there are no seams or other discontinuities that may cause amputee discomfort. A liner of the present invention may protect and cushion the entire portion of a residual limb residing in a prosthetic socket.

While a liner of the present invention may be of the cushion liner variety, other embodiments may be constructed as cushion locking liners. A liner of the present invention may include a connecting element (adapter) at the closed (distal) end for facilitating coupling of the liner to the socket of a prosthetic limb. Such connecting elements may be designed with an accordion shape that provides for increased comfort when the liner is worn by better conforming to the distal shape of the residual limb.

While certain embodiments of the present invention are described in detail above, the scope of the invention is not to be considered limited by such disclosure, and modifications are possible without departing from the spirit of the invention as evidenced by the following claims:

EXAMPLE

A series of gel compositions were explored. The gel compositions were formulated with an amount of SEPTON™ J hydrogenated block copolymer, mineral oil as a plasticizing oil, and one or more of: SEPTON 4033 SEEPS thermoplastic elastomer, SEPTON 4055 SEEPS thermoplastic elastomer, SEPTON 8004 SEBS thermoplastic elastomer, polyethylene (PE) as a hardening agent, and polypropylene (PP) as a hardening agent. The compositions and properties of the gel examples are shown in FIG. 10, Table 6.

The gel compositions formulated with an amount of SEEPS thermoplastic elastomer demonstrated an increase in Shore 00 hardness (durometer) with respect to gel compositions formulated with only hydrogenated block copolymer SEPTON™ J. The addition of a hardening agent to formulations including a SEEPS thermoplastic elastomer further increased the durometer value. However, gel compositions formulated with an amount of SEBS thermoplastic elastomer, in the absence of hardening agent, provided the greatest durometer value, though at the expense of tear and tensile strength.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the terms "operatively coupled" or "operatively connected" are used in the specification or the claims, it is intended to mean that the identified components are connected in a way to perform a designated function. To the extent that the term "substantially" is used in the specification or the claims, it is intended to mean that the identified components have the relation or qualities indicated with degree of error as would be acceptable in the subject industry.

As used in the specification and the claims, the singular forms "a," "an," and "the" include the plural unless the singular is expressly specified. For example, reference to "a compound" may include a mixture of two or more compounds, as well as a single compound.

As used herein, the term "about" in conjunction with a number is intended to include ±10% of the number. In other words, "about 10" may mean from 9 to 11.

As used herein, the terms "optional" and "optionally" mean that the subsequently described circumstance may or may not occur, so that the description includes instances where the circumstance occurs and instances where it does not.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The various aspects and embodiments disclosed herein are for purposes of illustration and are not intended to be limiting, with the true scope and spirit being indicated by the following claims.

The invention claimed is:

1. A prosthetic cushion liner, comprising:
a fabric covering having an open end for introduction of a residual limb and a closed end opposite the open end; and
a continuous layer of a gel composition residing on an interior surface of the fabric covering, the gel composition comprising:
a plasticizing oil;
a hardening agent;
one or more of:
a thermoplastic elastomer represented by Formula II

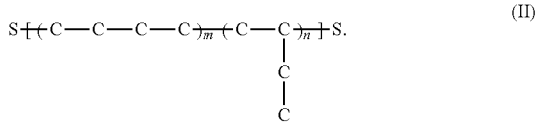
(II)

wherein C is a Carbon and m and n represent a number of repeats,
a thermoplastic elastomer represented by Formula III

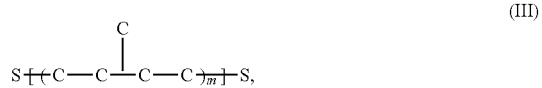
(III)

wherein C is Carbon and m represents a number of repeats, and
a thermoplastic elastomer represented by Formula IV

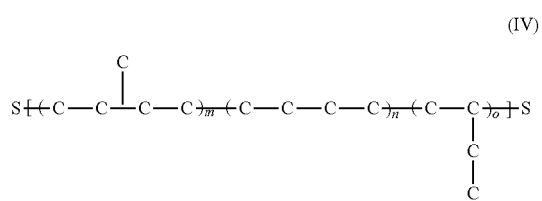
(IV)

wherein C is a Carbon and m, n, and o represent a number of repeats; and
a hydrogenated block copolymer derived from a living polymer represented by Formula (I):

(I)

wherein:
A is a polymer block comprising a structural unit derived from a vinyl aromatic compound;
$B_1$ and $B_2$ are each a polymer block comprising a structural unit derived from a conjugated diene compound; and
X is a linking group derived from reaction of an active terminal end of the having polymer with a coupling agent.

2. The prosthetic cushion liner of claim 1, the vinyl aromatic compound comprising styrene.

3. The prosthetic cushion liner of claim 1, the conjugated diene compound comprising one or more of: isoprene and 1,3-butadiene.

4. The prosthetic cushion liner of claim 1, the coupling agent comprising one or more of: divinyl benzene, a polyvalent epoxy compound, a halogenated silane compound, a halogenated tin compound, an ester compound, a carbonate ester compound, and an alkoxysilane compound.

5. The prosthetic cushion liner of claim 1, the gel composition characterized by hydrogenation of at least 80% of alkene bonds corresponding to the conjugated diene compound from which $B_1$ and $B_2$ are derived.

6. The prosthetic cushion liner of claim 1, the plasticizing oil comprising mineral oil.

7. The prosthetic cushion liner of claim 1, the plasticizing oil being present in the gel composition in an amount between about 75 weight percent and about 85 weight percent.

8. The prosthetic cushion liner of claim 1, the hardening agent comprising one or more of: polyethylene, styrene oligomers, and polypropylene.

9. The prosthetic cushion liner of claim 1, the hardening agent comprising polyethylene in an amount between about 0.1 weight percent and about 1.5 weight percent.

10. The prosthetic cushion liner of claim 1, the hydrogenated block copolymer being characterized by a styrene content of about 37 to about 47 weight percent.

11. The prosthetic cushion liner of claim 1, the hydrogenated block copolymer being characterized by a specific gravity of about 0.90 to about 0.95.

12. The prosthetic cushion liner of claim 1, the hydrogenated block copolymer being present in the gel composition in an amount between about 3 weight percent and about 25 weight percent.

13. The prosthetic cushion liner of claim 1, the gel composition comprising the thermoplastic elastomer represented by Formula IV.

14. The prosthetic cushion liner of claim 13, the thermoplastic elastomer being characterized by a styrene content of between about 27 weight percent and about 35 weight percent.

15. The prosthetic cushion liner of claim 13, the thermoplastic elastomer being characterized by a specific gravity of about 0.90 to about 0.95.

16. The prosthetic cushion liner of claim 13, the thermoplastic elastomer being present in the gel composition in an amount between about 3 weight percent and about 20 weight percent.

17. The prosthetic cushion liner of claim 13, the hydrogenated block copolymer and the thermoplastic elastomer being present in the gel composition in a ratio of about one of: 11:1, 6:1, 5:1, 1:1, 1:2, 1:4, and 1:7.

18. The prosthetic cushion liner of claim 1, the gel composition comprising the thermoplastic elastomer represented by Formula II.

19. The prosthetic cushion liner of claim 18, the thermoplastic elastomer being characterized by a styrene content between about 27 weight percent and about 65 weight percent.

20. The prosthetic cushion liner of claim 18, the thermoplastic elastomer being characterized by a specific gravity between about 0.90 to about 0.98.

21. The prosthetic cushion liner of claim 18, the hydrogenated block copolymer and the thermoplastic elastomer being present in the gel composition in a ratio of about one of: 11:1, 6:1, 5:1, 3:1, 2:1, 1:1, 1:2, 1:4, and 1:7.

22. The prosthetic cushion liner of claim 1, the gel composition being characterized by a Shore 00 hardness of between about 10 and about 35.

23. The prosthetic cushion liner of claim 1, further comprising a docking element attached to the fabric covering at the closed end for coupling the prosthetic cushion locking liner to a socket portion of a prosthetic limb.

* * * * *